United States Patent [19]

Göbel et al.

[11] Patent Number: 5,936,112
[45] Date of Patent: Aug. 10, 1999

[54] MIXTURES CONSISTING OF BIS (SILYLORGANYL) POLYSULFANS AND SILYORGANYLTHIOCYANATES, THEIR PRODUCTION, AND USE

[75] Inventors: Thomas Göbel, Hanau; Ulrich Deschler, Sailauf; Jörg Münzenberg; Gerd Zezulka, both of Hanau, all of Germany

[73] Assignee: Degussa Aktiengesellschaft, Frankfurt am Main, Germany

[21] Appl. No.: 09/113,151

[22] Filed: Jul. 10, 1998

[30] Foreign Application Priority Data

Jul. 30, 1997 [DE] Germany .................. 197 32 725

[51] Int. Cl.⁶ ................... C07F 7/08; C07F 7/10; C08K 9/06
[52] U.S. Cl. .................. 556/427; 152/151; 523/209; 523/213; 523/215; 523/216; 525/102; 525/342; 525/351; 525/352
[58] Field of Search ............... 556/427; 523/209, 523/213, 215, 216; 525/102, 342, 351, 352; 152/151

[56] References Cited

U.S. PATENT DOCUMENTS

| | | | |
|---|---|---|---|
| 3,873,489 | 3/1975 | Thurn et al. | 556/427 |
| 3,997,581 | 12/1976 | Pletka et al. | 260/448.2 |
| 4,072,701 | 2/1978 | Pletka et al. | 260/448.8 |
| 4,128,438 | 12/1978 | Wolff et al. | 106/307 |
| 4,507,490 | 3/1985 | Panster | 556/427 |
| 4,981,937 | 1/1991 | Kuriyama et al. | 526/328 |
| 5,116,886 | 5/1992 | Wolff et al. | 523/209 |
| 5,405,985 | 4/1995 | Parker | 556/427 |
| 5,466,848 | 11/1995 | Childress | 556/427 |
| 5,489,701 | 2/1996 | Childress et al. | 556/427 |
| 5,596,116 | 1/1997 | Childress et al. | 556/427 |
| 5,663,396 | 9/1997 | Musleve et al. | 556/427 |

FOREIGN PATENT DOCUMENTS 2186060  3/1997  Canada .

*Primary Examiner*—Paul F. Shaver
*Attorney, Agent, or Firm*—Beveridge, DeGrandi, Weilacher & Young, L.L.P.

[57] ABSTRACT

Mixtures are disclosed of bis(silylorganyl)polysulfanes and silylorganylthiocyanates, which are produced by reacting polysulfanes with cyanides. The inorganic thiocyanate formed is subsequently allowed to react with a haloalkylalkoxysilane to form the silylorganylthiocyanate. These substances are used in plastic and rubber mixtures reinforced with silica and optionally carbon black.

21 Claims, No Drawings

MIXTURES CONSISTING OF BIS (SILYLORGANYL) POLYSULFANS AND SILYORGANYLTHIOCYANATES, THEIR PRODUCTION, AND USE

INTRODUCTION AND BACKGROUND

The present invention relates to mixtures of bis(silylorganyl)polysulfanes and silylorganylthiocyanates, as well as their preparation and use in rubber mixtures.

Trialkoxysilylpropylpolysulfanes are excellent bonding agents for the incorporation of oxide material into rubber matrices. Particularly in the tire industry, the bis(triethoxysilylpropyltetrasulfane ([C$_2$H$_5$O)$_3$Si(CH$_2$)$_3$]$_2$S$_4$] is widely used in silica reinforced tires. There is a binding of the silane to the free hydroxyl groups of the silicic acid, on the one hand, and a vulcanization-like crosslinking with the rubber, on the other hand. For special uses, it is advantageous not to equip the silane with a tetrasulfane function but rather with a less reactive disulfane function. The synthesis of silylalkyldisulfanes is described together with their corresponding polysulfanes in various patents and publications.

German Patent Nos. 2,405,758 and 2,542,534 concern the preparation, proceeding from mercaptoalkyl silanes and sulfur, in which 1 hydrogen sulfide is released.

Several preparation methods are based on in-situ-produced disulfides, with which nucleophilic substitutions are then carried out on haloalkylsilanes. These methods differ only in the synthesis of the nucleophilic disulfide. According to German Patent No. 3,311,340, the disulfide is produced by reactions between hydrogen sulfide, sodium, and sulfur in ethanol.

According to U.S. Pat. No. 5,405,985, an aqueous sodium sulfide solution is used together with sulfur for the preparation. Persons skilled in the art are sufficiently aware that, during reactions between sulfides and sulfur, mixtures of various polysulfides are formed, so that during the nucleophilic substitution, in turn, only a mixture of polysulfanes with various chain lengths can result. The same is true for reactions between mercaptans or thiolates and sulfur. It is furthermore known that the corresponding disulfanes can be separated from these product mixtures only with great difficulty.

In German Patent No. 2,360,470, a method for the preparation of pure bis(silylalkyl)disulfane by the oxidation of the corresponding mercaptan with sulfuryl chloride is described, but strongly corrosive by-products (SO$_2$, HCl) are formed during this process. Secondary reactions on the silyl group also lead to a reduction of the yield of the desired product (example: 63.3%). Another oxidative variant is found in European Patent No. A1 217,178. Here, the corresponding thiolates are oxidized by iodine to form the disulfides. The process requires two more reaction steps after the expensive preparation of the silylalkylmercaptan.

In the unpublished German Patent application No. 195 41 404.7, a method for the selective synthesis of silylalkyldisulfanes is described.

In that document, polysulfanes are reacted for the desulfuration with nucleophilic reagents, such as NaCN. A disadvantage of this reaction, however, is to be found in the fact that per mol of the sulfur atoms to be removed, 1 mol of NaSCN is formed by the reaction with NaCN. This can be separated only in a cumbersome manner and then must be disposed of.

An object of the present invention is, above all, to avoid the inevitable yield of NaSCN that results from prior known processes.

SUMMARY OF THE INVENTION

The above as well as other objects of the invention are achieved by mixtures comprising of at least one bis(silylorganyl)polysulfane and at least one silylorganyl thiocyanate of the following formula:

$$(R^1R^2R^3SiR^4)_xX$$

in which the meanings are as follows:

x is an integer of 1 or 2, and when x is 2,
then X is S$_n$, with n being a whole number from 2–20, in particular from 2–8, and when x is 1
then X is SCN, R$^1$, R$^2$, R$^3$ are the same or different from one another, and are branched or unbranched, alkyl and/or alkoxy groups with a chain length of 1–8 C atoms, preferably 1–3 C atoms, with the proviso that at least one of R$^1$, R$^2$, and R$^3$, is an alkoxy group, preferably 3 alkoxy groups, hydrogen atom, or a 10 monovalent aryl radical, in particular phenyl, toluyl, or benzyl; and R$^4$ is a divalent alkylidene radical with a chain length of 1–8 C atoms, preferably 2–4 C atoms, or

with y=1–4.

Preferred mixtures in accordance with the present invention are those that comprise polysulfanes and thiocyanates according to formula (I) and in which R$^1$, R$^2$, R$^3$, and R$^4$ have the same meanings in both compounds, but without each of R$^1$, R$^2$, and R$^3$, having to be the same.

Polysulfanes and thiocyanates according to formula (I) are preferably present in a mole ratio of 1:20 to 20:1. Particularly preferred are mixtures that comprise bis(trialkoxysilylpropyl)disulfanes and thiocyanatopropyltrialkoxysilanes, in particular the methoxy or ethoxy compounds.

Small quantities of starting material compounds according to formula (IV) are not taken into consideration here.

The mixtures in accordance with the invention are suitable, in particular, for the improvement of the application-technical characteristics of plastic and rubber mixtures reinforced with a filler, in particular silica.

This mixture represents, for the first time, a combination of organosilicon compounds, known only in single applications in the rubber industry.

Whereas these compounds have been understood as competitive substances up to now (European Patent No. A 0,764,687), surprising results have been achieved with the combined use of disulfanes and thiocyanatosilanes.

A feature of the present invention is the method for the preparation of these mixtures, which is characterized in that silylorganylpolysulfanes or their mixtures according to the following formula:

$$(R^1R^2R^3SiR^4)_2S_n, \quad \text{(II)}$$

in which R$^1$, R$^2$, R$^3$, R$^4$, and n (excluding n=2) have the same meaning as in formula (I), are reacted with a nucleophilic compound of the following formula:

$$M^+CN^-, \quad \text{(III)}$$

in which the meanings are as follows:

M$^+$ is an alkali cation, in particular Na$^+$, a substituted or unsubstituted ammonium ion or represents half of an alkaline earth or zinc ion, wherein the compounds are preferably used, in accordance with formula (III), in an equimolar relation to the number of sulfur atoms to be removed from the compound in accordance with formula (II). The resulting reaction mixture is reacted with a compound of the following formula:

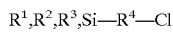

R$^1$,R$^2$,R$^3$,Si—R$^4$—Cl in which R$^1$, R$^2$, R$^3$, and R$^4$ have the same meaning as in formula (I), in the mole ratio of 0.05:1 to 1.0:1, with reference to the compound in accordance with formula (III), at an elevated temperature under pressure. After the reaction, the mixture of the desired compounds can be separated.

Only NaCl, which can be separated and disposed of without any problems, is formed in the method of this invention as a by-product.

Unreacted quantities of compounds according to formula (IV) are not a problem in the further use of the mixtures and are, optionally, components of the mixtures in accordance with the invention.

DETAILED DESCRIPTION OF THE INVENTION

The present invention will now be described in further detail with specific embodiments.

The method can be carried out both in a solvent-free system as well as with the addition of solvents. Preferred are those solvents in which the nucleophilic compound used is at least partially soluble.

Aliphatic solvents such as pentane, hexane, or mixtures of various branched and unbranched alkanes or aromatic solvents, such as benzene, toluene, or xylene, or ethers such as diethyl ether, dibenzyl ether, methyl-tert-butyl ether, can be used. The organic solvents used are generally inert under the selected reaction conditions.

Preferably, a linear or branched alcohol with 1–8 C atoms, such as methyl, ethyl, propyl, butyl, or pentyl alcohol, can be used as the organic solvent. Also suitable are cycloalkyl alcohols with 5–8 C atoms, such as phenol or benzyl alcohol.

Particularly suitable, so as to avoid, for example, a transesterification, are the alcohols corresponding to groups R$^1$, R$^2$, and R$^3$ (alkoxy) which can be used. Optionally, the use of a mixture of these alcohols can also be advantageous—for example, if R$^1$, R$^2$, and R$^3$ are not the same in a given compound.

The reaction of thiocyanatosilane is advantageously carried out at a temperature of 20° C. up to the boiling temperature of the solvent(s) used, preferably under pressure. This is 1000–5000 hpa, preferably 1500–3500 hpa.

In an advantageous specific embodiment, a tetrasulfane according to formula (II) or a mixture of polysulfanes according to formula (II), whose statistical sulfur mean value corresponds to a tetrasulfane, is reacted with a cyanide according to formula (III) to form a disulfane. The formed thiocyanate salt is then reacted, as described, with a sufficient quantity of the compound according to formula (IV) added to the desired mixture. This preferably contains a disulfane and a silylorganylthiocyanate in the mole ratio of 1:2.

It was also discovered that the polysulfane, in particular the tetrasulfane, need not be prepared separately according to formula (II), so as to be able to subsequently use it in the method for the preparation of the mixtures in accordance with the invention.

It is instead possible to use an "in situ" method. This means that the desulfurated organosilane is not prepared separately, but rather is produced "in situ" and can be further reacted immediately (one-pot reaction).

In order to obtain mixtures in accordance with the invention, only the solvent, which is optionally used, and the NaCl formed still have to be separated.

For this purpose, solutions in an organic solvent, or optionally suspensions are prepared that contain:

a) silylorganylpolysulfanes or their mixtures according to formula (II);

b) a nucleophilic compound of the following formula:

M$^+$CN$^-$                                         (III); and c) an organosilicon compound of the following formula:

Cl—R$^4$—SiR$^1$R$^2$R$^3$,                       (IV)

in a mole ratio of a:b:c of (n−2):k(n−2):m(n−2), wherein 0<k≦1; k·0.05≦m≦k; n>2. Meanings of symbols are otherwise the same as above.

The reaction is preferably carried out in a temperature-controlled manner. This means that at the beginning, a temperature range of 30–85° C. is maintained. After 20 the desulfuration, the temperature is increased, so that the mixtures are formed in accordance with the invention.

This range lies, in particular, between 90 and 150° C. under a pressure of 1000–5000 hpa.

The methods in accordance with the invention permit the composition of the mixtures to vary to a great extent.

The S$_n$ groups according to formula (I) as well as the quantity of thiocyanatosilane to be formed as a result of the desulfuration and the subsequent reaction of the formed alkali metal thiocyanate with the compound according to formula (IV) can be adjusted as desired.

This depends on the characteristics desired for the vulcanized material produced using the mixtures in accordance with the invention, or under the selected conditions for carrying out the vulcanization.

It is namely known that, for example, the number of sulfur atoms in the polysulfanes greatly influence the scorch behavior of, in particular, rubber mixtures that can be vulcanized with sulfur or sulfur compounds.

For this reason, it is sometimes useful to add disulfanes and/or thiocyanatosilanes of the aforementioned formulas to the mixtures thus produced, or to do this during the production of vulcanizable rubber mixtures, if the desired characteristics of the vulcanized material appear to make it necessary.

The mixtures in accordance with the invention are preferably mixed with the silica or caused to react before mixing into the rubber mixtures, as described, for example, in U.S. Pat. No. 5,116,886 (European Patent No. B 0,442,143).

Small quantities of unreacted compounds according to formula (IV) do not have a disadvantageous effect on the characteristics of the vulcanized materials.

It is not absolutely necessary to modify the entire quantity of silica used beforehand with one of the mixtures according to the invention. It is also possible to modify only a part thereof. It is also possible to modify, in advance, only one part and to use the rest without prior modification, and to subsequently admix the remaining quantity of the mixture with the rubber.

If carbon black is intended as an additional filler for the rubber mixture to be produced, there is, in another variant, the possibility of using the organosilane mixture, entirely or in part, in a formulation with carbon black. This is then preferably used in the form of a granulate with a content of 30–60 wt % of organosilanes or 70–40 wt % of carbon black. The production of similar granulates is described in German Patent No. 2,747,277 (U.S. Pat. No. 4,128,438) and can be carried out in an analogous manner here.

The use of organosilane mixtures in accordance with the invention with a weight distribution of 60:40 to 90:10, preferably 75:25 to 85:15 (disulfane:thiocyanatosilane), in particular, but approximately 80:20, has proved to be particularly advantageous.

Compared with the characteristics of vulcanized materials produced using disulfanes as the sole silicon-organic compound, in particular vulcanized materials in whose production the aforementioned mixtures are used, prove to be superior with regard to the modulus (DIN 53504), the wear resistance (DIN 53516), the heat buildup (ASTM D 623 A), and the loss factor tan δ at 60° C. (DIN 53 513).

The following examples are illustrative of the present invention.

EXAMPLE 1

Production of a mixture of disulfane and thiocyanatosilane 137.4 g (0.25 mol) of bis(3,3'-triethoxysilylpropyl) tetrasulfane are reacted in 150 mL of ethanol with 23.28 g (0.48 mol) of sodium cyanide under reflux in a glass apparatus, consisting of a 1-L three-necked flask with a reflux condenser. After stirring for 3 h under reflux, the reaction mixture is cooled and transferred to an autoclave. The reaction flask is rinsed with 50 mL of ethanol and the rinsing solution is added to the autoclave contents, together with 102.34 g (0.43 mol) of 3-chloropropyltriethoxysilane. After closing the autoclave, heating is carried out to 120° C. for 7 h. After cooling the autoclave contents to room temperature, the mixture formed is filtered and the solvent is removed from the filtrate in a vacuum of 15 mbar. The residue contains a mixture of rubber-reactive silanes (bis(3,3'-triethoxysilylpropyl)polysulfanes and 3-thiocyanatopropyltriethoxysilane at a yield of 82% according to the $^1$H-NMR spectrum.

The following distribution is produced:
Disulfane: 73 wt %
Thiocyanatosilane: 18 wt %
Chloropropylsilane: 9 wt %

EXAMPLE 2

Production of a mixture of disulfane and thiocyanatosilane (one-pot reaction)

A mixture of 137.4 g (0.25 mol) of bis(3,3'-triethoxysilylpropyl)tetrasulfane, 23.28 g (0.48 mol) of sodium cyanide, and 102.34 g (0.43 mol) of 3-chloropropyltriethoxysilane in 200 mL of ethanol is placed in a 500-mL autoclave. Heating is carried out at 85° C. for 3 h and subsequently at 120° C. for 8 h, then cooling after the reaction time. The reaction mixture is filtered, the solvent is removed from the filtrate in a vacuum (15 mbar), and the residue is evaluated from its $^1$H-NMR spectrum. A mixture of rubber-reactive silanes is obtained at a yield of 76%.

The following distribution is produced:
Disulfane: 76 wt %
Thiocyanatosilane: 12 wt %

Further variations and modifications will be apparent to those skilled in the art from the foregoing and are intended to be encompassed by the claims appended hereto.

German priority application 197 32 725.7 is relied on and incorporated herein by reference.

We claim:

1. A mixture comprising a bis(silylorganyl)polysulfane and a silylorganylthiocyanate of the following formula:

   (I), in which the meanings are as follows:
wherein x is 1 or 2, and when x is 2, then X is $S_n$ with n equal to a whole number from 2–20, and when x is 1, then X is SCN, $R^1$, $R^2$, $R^3$ are the same or different from one another, branched or unbranched, alkyl or alkoxy groups with a chain length of 1–8 C atoms or mixtures thereof, hydrogen or monovalent aryl, provided that at least one of $R^1$, $R^2$, and $R^3$, is alkoxy, hydrogen, or a monovalent aryl; and $R^4$ is divalent alkylidene with a chain length of 1–8 C atoms or

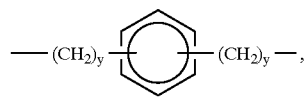

with y=1–4.

2. The mixture according to claim 1 wherein n is 2 to 8.

3. The mixture according to claim 1 wherein said monovalent aryl is phenyl, toluyl or benzyl.

4. The mixture according to claim 1 wherein $R^4$ is divalent alkylidene with 2 to 4 C atoms.

5. The mixture according to claim 1, which comprises a polysulfane and thiocyanate according to formula (I), and in which $R^1$, $R^2$, $R^3$, and $R^4$ have the same meanings in both compounds.

6. The mixture according to claim 1, which comprises a polysulfane and a thiocyanate according to formula (I) in a mole ratio of 1:20 to 20:1.

7. The mixture according to claim 1, comprising bis(trialkoxysilylpropyl)disulfane and thiocyanatopropyltri-alkoxysilane in a weight ratio of 60:40 to 90:10.

8. The mixture according to claim 7 in a weight ratio of 75:25 to 85:15.

9. The mixture according to claim 1, which also contains silica and/or carbon black in a quantity of 5–95 wt %.

10. A method for the preparation of a desired mixture of compounds according to claim 1, comprising reacting a silylorganylpolysulfane or a mixture in accordance with the following formula:

   (II)

in which $R^1$, $R^2$, $R^3$, $R^4$, and n have the same meaning as in formula (I) excluding n=2, with a nucleophilic compound of the following formula:

   (III)

in which the meanings are as follows:

$M^+$ is an alkali metal cation, a substituted or unsubstituted ammonium ion or half of an alkaline earth or zinc ion, wherein the compound of formula (III) is in an equimolar relation to the number of sulfur atoms to be removed from the compound formula (II); wherein the resulting reaction mixture is reacted with a compound of the formula:

   (IV)

in which $R^1$, $R^2$, $R^3$, and $R^4$ have the same meaning as in formula (I), in a mole ratio of 0.05:1 to 1.0:1, with reference to the compound of formula (III), at an elevated temperature under pressure, to obtain said desired mixture of compounds and optionally separating said desired mixture of compounds from the reaction mixture.

11. The method according to claim 10, characterized in that the compounds according to formulas (II), (III), and (IV) are mixed with one another in the desired mole ratios, then reacted under pressure at an elevated temperature to form a reaction mixture; and then separating the desired mixture of compounds from the reaction mixture.

12. The method according to claim 10 wherein a mixture is formed comprising:

a) silylorganylpolysulfane or a mixture in accordance with formula (II) and the compound b) M⁺CN⁻ (III), and c) an organosilicon compound of the following general formula:

    (IV)

in which a:b:c are present in a mole ratio of (n−2):k(n−2):m(n−2), wherein 0<k≦1; k·0.05≦m≦k; n>2, and otherwise the meanings are the same as above; with said mixture being present as a solution or suspension, converting said mixture at a temperature of 30–85° C. to a conversion mixture and subsequently heating the conversion mixture to an elevated temperature and under pressure, to thereby form said desired mixtures of compounds, and optionally separating said desired mixture of compounds for recovery thereof.

13. The method according to claim 10, wherein a tetrasulfane or a compound in which the statistical mean of n corresponds to four is used.

14. The method according to claim 10, wherein a polysulfane or a mixture of polysulfanes according to formula (II) is reacted with the corresponding disulfane.

15. A method for the production of a vulcanizable plastic or rubber reinforced with silica and, optionally, carbon black, comprising mixing the desired mixture of compounds according to claim 1 into said plastic or rubber.

16. The method according to claim 15, wherein the desired mixture of compounds comprises bis(trialkoxysilylpropyl)disulfane and thiocyanatopropyltrialkoxysilane in a weight ratio of 60:40 to 90:10.

17. The method according to claim 15, wherein the desired mixture of compounds comprises bis(trialkoxysilylpropyl)disulfane and thiocyanatopropyltrialkoxysilane is used in a weight ratio of 75:25 to 85:15.

18. The method according to claim 15, wherein a disulfane according to formula (II) and/or a thiocyanatosilane according to formula (I) wherein X is SCN and x=1 is added to said desired mixture of compounds.

19. A vulcanizable plastic or rubber made by the method of claim 15.

20. A vulcanizable plastic or ribber made by vulcanizing the plastic or rubber of claim 19.

21. A tire for a vehicle made from the vulcanized plastic or rubber of claim 20.

* * * * *